(12) United States Patent
Ludwig et al.

(10) Patent No.: US 9,517,292 B2
(45) Date of Patent: Dec. 13, 2016

(54) POLYMER FOR CREATING HEMOCOMPATIBLE SURFACE

(71) Applicant: Abbott Cardiovascular Systems Inc., Santa Clara, CA (US)

(72) Inventors: Florian N. Ludwig, Hilversum (NL); John Stankus, Campbell, CA (US); Mikael Trollsas, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/167,677

(22) Filed: Jan. 29, 2014

(65) Prior Publication Data

US 2014/0147485 A1 May 29, 2014

Related U.S. Application Data

(62) Division of application No. 12/397,154, filed on Mar. 3, 2009, now Pat. No. 8,668,919.

(51) Int. Cl.
| | |
|---|---|
| *A61K 9/127* | (2006.01) |
| *A61K 47/44* | (2006.01) |
| *A61P 33/06* | (2006.01) |
| *C12N 5/071* | (2010.01) |
| *C07C 51/347* | (2006.01) |
| *A61K 39/015* | (2006.01) |
| *A61L 31/10* | (2006.01) |
| *A61L 29/08* | (2006.01) |
| *A61L 33/06* | (2006.01) |
| *A61K 31/436* | (2006.01) |
| *A61K 47/32* | (2006.01) |
| *A61L 31/16* | (2006.01) |
| *C08F 220/28* | (2006.01) |

(52) U.S. Cl.
CPC .............. *A61L 31/10* (2013.01); *A61K 31/436* (2013.01); *A61K 47/32* (2013.01); *A61L 29/085* (2013.01); *A61L 31/16* (2013.01); *A61L 33/06* (2013.01); *C08F 220/28* (2013.01); *Y10T 428/31935* (2015.04)

(58) Field of Classification Search
CPC ..... A61K 31/436; A61K 47/32; A61L 29/085; A61L 33/06; C08F 220/28
See application file for complete search history.

(56) References Cited

U.S. PATENT DOCUMENTS

| | | | |
|---|---|---|---|
| 2005/0208093 A1* | 9/2005 | Glauser et al. ............... | 424/423 |
| 2005/0255142 A1* | 11/2005 | Chudzik et al. .............. | 424/426 |
| 2007/0292518 A1* | 12/2007 | Ludwig .................. | A61B 18/04 |
| | | | 424/489 |

OTHER PUBLICATIONS

Ye et al. (Wiley Interscience, JBMA.a.32184; pp. 18-28; Published online Aug. 5, 2008.*

* cited by examiner

*Primary Examiner* — Anna Falkowitz
(74) *Attorney, Agent, or Firm* — Squire Patton Boggs (US) LLP

(57) ABSTRACT

A polymer comprising a phosphoryl choline moiety(ies), a composition comprising the polymer and optionally a bioactive agent, an implantable device such as a DES or a non-implantable device such as an angioplasty balloon comprising thereon a coating comprising the polymer and optionally a bioactive agent, and a method of using the device for the treatment of a disorder in a human being are provided.

6 Claims, No Drawings

POLYMER FOR CREATING HEMOCOMPATIBLE SURFACE

CROSS-REFERENCE TO RELATED APPLICATION

This application is a divisional application of U.S. application Ser. No. 12/397,154 filed on Mar. 3, 2009, the teaching of which is incorporated by reference in its entirety herein.

BACKGROUND OF THE INVENTION

Field of the Invention

This invention generally relates to a polymeric composition comprising at least one phosphoryl choline moiety that is useful for coating an implantable device such as a drug eluting stent.

Description of the Background

Implanted stents have been used to carry medicinal agents, such as thrombolytic agents. U.S. Pat. No. 5,163,952 to Froix discloses a thermal-memoried expanding plastic stent device formulated to carry a medicinal agent in the material of the stent itself. Pinchuk, in U.S. Pat. No. 5,092,877, discloses a stent of a polymeric material which may have a coating associated with the delivery of drugs. Other patents which are directed to devices of the class utilizing bio-degradable or bio-absorbable polymers include Tang et al., U.S. Pat. No. 4,916,193, and MacGregor, U.S. Pat. No. 4,994,071.

Blood vessel occlusions are commonly treated by mechanically enhancing blood flow in the affected vessels, such as by employing a stent. Stents are used not only for mechanical intervention but also as vehicles for providing biological therapy, e.g., a controlled delivery of agents. To effect a controlled delivery of an active agent in stent based therapy, the stent can be coated with a biocompatible polymeric coating. The biocompatible polymeric coating can function either as a permeable layer or a carrier to allow a controlled delivery of the agent. A continuing challenge in the art of implantable stents is to provide a coating that possesses good biobeneficial properties, which refer to good biocompatibilities in both the acute and chronic timeframes.

Generally, a polymer forming a coating composition for an implantable device has to be at least biologically benign. The polymer is preferably biocompatible. To provide for a coating that is biologically benign, various compositions have been used with limited success.

The polymer and methods of making the polymer disclosed herein address the above described problems.

SUMMARY OF THE INVENTION

The polymeric compositions described herein can be used to form a coating on an implantable device such as a drug-eluting device (DES). The implantable device can be used for the treatment of a disorder in a human being by implanting in the human being an implantable device as described herein. Such a disorder includes, e.g., atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

In one embodiment, provided herein is a hydrophilic polymer having a biodegradable or nondegradable polymeric backbone capped by at least one phosphoryl choline moiety (PC) and a functional moiety F. The functional moiety F may be used to couple the polymer to an implantable medical device surface or coating, a protein, or a drug delivery vehicle comprising a chemical moiety R to which F binds or reacts.

In another embodiment, a polymer having a biodegradable or nondegradable polymeric backbone capped by at least one PC moiety and a functional moiety F. The functional moiety F may be used to couple the polymer to an implantable medical device surface or coating, a pritein, or a drug delivery vehicle comprising a chemical moiety R to which F binds or reacts.

In an additional embodiment, an amphiphilic polymer is biodegradable or nondegradable polymeric backbone capped by at least one PC moiety and a functional moiety F. The functional moiety F may be used to couple the polymer to an implantable medical device surface or coating, a protein, or a drug delivery vehicle comprising a chemical moiety R to which F binds or reacts.

In one embodiment, a hydrophilic polymer (LP) is capped at its one end by a PC moiety, and has a lipid molecule (LI) coupled to its other end. The LP can be used to form a coating on an implantable device such as a drug-eluting stent. The coating may optionally include one or more bioactive agents and/or a non-fouling polymer, an anti-thrombogenic polymer, or a combination thereof.

In another embodiment, a hydrophobic polymer PP is capped at its one end by a PC moiety, and has a LI coupled to its other end. The hydrophobic polymer PP capped by PC moiety(ies) can be used to form a coating on an implantable device such as a drug-eluting stent. The coating may optionally include one or more bioactive agents and/or a non-fouling polymer, an anti-thrombogenic polymer, or a combination thereof.

DETAILED DESCRIPTION

Described herein is a polymer comprising PC moiety(ies) and hydrophilic, hydrophobic or amphiphilic polymer segments or blocks.

PC has a zwitterionic functionality that mimics the outer blood-contacting surface of the lipid bilayer structure in blood corpuscles. PC possesses numerous biobeneficial properties such as hemocompatibility, non-thrombogenicity, arterial tissue acceptance and long-term in vivo stability. PC has been used to increase biocompatibility of polymers, especially that of acrylic copolymers.

This polymer may be used to coat drug delivery devices. Embodiments of this polymer are described below.

Coating Composition Comprising at Least a Phosphoryl Choline

In one embodiment, provided herein is a hydrophilic polymer having a biodegradable or nondegradable polymeric backbone capped by at least one PC moiety and a functional moiety F. The functional moiety F may be used to couple the polymer to a) an implantable medical device surface or coating comprising a chemical moiety R to which F binds or reacts; b) a protein comprising a chemical moiety R to which F binds or reacts; or c) a drug delivery vehicle such as a liposome, micelle, or a polymeric nanoparticle/micelle/microparticle the surface of which comprises a chemical moiety R to which F binds or reacts. The hydrophilic polymer above can be used to form a coating on an implantable device such as a drug-eluting stent. The coating may optionally include one or more bioactive agents and/or a non-fouling polymer, an anti-thrombogenic polymer, or a combination thereof.

In another embodiment, a hydrophobic polymer having a biodegradable or nondegradable polymeric backbone can be capped by at least one PC moiety and a functional moiety F. The functional moiety F may be used to couple the polymer to a) an implantable medical device surface or coating comprising a chemical moiety R to which F binds or reacts; b) a protein comprising a chemical moiety R to which F binds or reacts; or c) a drug delivery vehicle such as a liposome, micelle, or a polymeric nanoparticle/micelle/microparticle the surface of which comprises a chemical moiety R to which F binds or reacts. The hydrophobic polymer capped by PC has a hydrophobic segment PP and can be used to form a coating on an implantable device such as a drug-eluting stent. The coating may optionally include one or more bioactive agents and/or a non-fouling polymer, an anti-thrombogenic polymer, or a combination thereof. In an embodiment, the hydrophobic segment PP may have a photoreactive moiety conjugated to them which may be activated after coating the polymer onto the device surface to chemically react the polymer to the surface of the device.

In an additional embodiment, an amphiphilic polymer having a biodegradable or nondegradable polymeric backbone is capped by at least one PC moiety and a functional moiety F. The PC capped amphiphilic polymer includes LP and PP segments. The functional moiety F may be used to couple the polymer to a) an implantable medical device surface or coating comprising a chemical moiety R to which F binds or reacts; b) a protein comprising a chemical moiety R to which F binds or reacts; or c) a drug delivery vehicle such as a liposome, micelle, or a polymeric nanoparticle/micelle/microparticle the surface of which comprises a chemical moiety R to which F binds or reacts. The amphiphilic polymer can be used to form a coating on an implantable device such as a drug-eluting stent. The coating may optionally include one or more bioactive agents and/or a non-fouling polymer, an anti-thrombogenic polymer, or a combination thereof. In an embodiment, the hydrophobic segment PP may have a photoreactive moiety conjugated to them which may be activated after coating the polymer onto the device surface to chemically react the polymer to the surface of the device.

In some embodiments, in the amphiphilic polymer, the PP segment comprises a hydrophobic component such as polylactide (PLA), poly(L-lactide) (PLLA), poly(D,L-lactide-co-glycolide) (PLGA), poly(e-caprolactone) (PCL), poly (ester amide) (PEA), polycarbonates, parylene, polytetrafluoroethylene (PTFE), polyvinylidene fluoride (PVDF), polyurethane (PU). In some embodiments, the LP segment comprises a hydrophilic component such as polyethylene glycol (PEG), polyvinylpyrrolidone (PVP), polyvinyl alcohol (PVA), polyvinyl pyrrolidon co-vinyl acetate (PVP-co-VA), pluronic polymers, and combinations thereof.

In one embodiment, a hydrophilic polymer LP is capped at its one end by a PC moiety, and has a lipid molecule LI coupled to its other end. The hydrophilic polymer can be used to form a coating on an implantable device such as a drug-eluting stent. The coating may optionally include one or more bioactive agents and/or a non-fouling polymer, an anti-thrombogenic polymer, or a combination thereof. In an embodiment, the hydrophobic segments of LI may have a photoreactive moiety conjugated to them which may be activated after coating the polymer onto the device surface to chemically react the polymer to the surface of the device.

In another embodiment, a hydrophobic polymer PP is capped at its one end by a PC moiety, and has a lipid molecule (LI) coupled to its other end. The hydrophobic polymer can be used to form a coating on an implantable device such as a drug-eluting stent. The coating may optionally include one or more bioactive agents and/or a non-fouling polymer, an anti-thrombogenic polymer, or a combination thereof. In an embodiment, the lipid molecule (LI) may have a photoreactive moiety conjugated to it which may be activated after coating the polymer onto the device surface to chemically react the polymer to the surface of the device.

Di- and Tri-Block Copolymers Comprising Phosphoryl Choline Moieties

According to another aspect of the present invention, provided is a block copolymer comprising hydrophilic block(s) (LP) and hydrophobic block(s) (PP) capped by PC moiety(ies).

One embodiment is directed to a di-block amphiphilic copolymer comprising a hydrophilic polymer block LP and a hydrophobic polymer block PP which is capped at its hydrophilic end by a PC moiety. The di-block amphiphilic copolymer can be used to form a coating on an implantable device such as a drug-eluting stent. The coating may optionally include one or more bioactive agents and/or a non-fouling polymer, an anti-thrombogenic polymer, or a combination thereof. In an embodiment, the hydrophobic polymer block PP may have a photoreactive moiety conjugated to them which may be activated after coating the polymer onto the device surface to chemically react the polymer to the surface of the device.

Another embodiment is directed to a di-block amphiphilic copolymer comprising a hydrophilic polymer block LP and a hydrophobic polymer block PP which is capped at its hydrophobic end by a PC moiety. The di-block amphiphilic copolymer can be used to form a coating on an implantable device such as a drug-eluting stent. The coating may optionally include one or more bioactive agents and/or a non-fouling polymer, an anti-thrombogenic polymer, or a combination thereof. In an embodiment, the hydrophobic polymer block PP may have a photoreactive moiety conjugated to them which may be activated after coating the polymer onto the device surface to chemically react the polymer to the surface of the device.

Yet another embodiment is a tri-block amphiphilic copolymer with a hydrophobic polymer block PP flanked on each side by a hydrophilic polymer block LP, both of which are capped at their respective ends by a PC moiety. The tri-block amphiphilic copolymer can be used to form a coating on an implantable device such as a drug-eluting stent. The coating may optionally include one or more bioactive agents and/or a non-fouling polymer, an anti-thrombogenic polymer, or a combination thereof. In an embodiment, the hydrophobic polymer block PP may have a photoreactive moiety conjugated to them which may be activated after coating the polymer onto the device surface to chemically react the polymer to the surface of the device.

An embodiment is a tri-block amphiphilic copolymer with a hydrophilic polymer block LP flanked on each side by a hydrophobic polymer block PP, both of which are capped at their respective ends by a PC moiety. The tri-block amphiphilic copolymer can be used to form a coating on an implantable device such as a drug-eluting stent. The coating may optionally include one or more bioactive agents and/or a non-fouling polymer, an anti-thrombogenic polymer, or a combination thereof. In an embodiment, the hydrophobic polymer block PP may have a photoreactive moiety conjugated to them which may be activated after coating the polymer onto the device surface to chemically react the polymer to the surface of the device.

Hydrophobic and Hydrophilic Polymers

In one embodiment, the hydrophilic polymers useful for making the polymers disclosed herein are polyethylene glycol (PEG), polyvinylpyrrolidone (PVP), polyvinyl alcohol (PVA), polyvinyl pyrrolidon co-vinyl acetate (PVP-co-VA), a Pluronics polymer, and combinations thereof.

In an embodiment, the hydrophobic polymers useful for making the polymers disclosed herein are polylactide (PLA), poly(L-lactide) (PLLA), poly(D,L-lactide-co-glycolide) (PLGA), poly(e-caprolactone) (PCL), poly(ester amide) (PEA), polycarbonates, parylene, polytetrafluoroethylene (PTFE), polyvinylidene fluoride (PVDF), polyurethane (PU), and combinations thereof.

Additional hydrophobic and hydrophilic biodegradable polymers include, but are not limited to, polyesters, polyhydroxyalkanoates (PHAs), poly(ester amides) that may optionally contain alkyl; amino acid; poly(D,L-lactide-co-PEG) block copolymers, poly(D,L-lactide-co-trimethylene carbonate), polyglycolide, polydioxanone (PDS), polyorthoester, polyanhydride, poly(glycolic acid-co-trimethylene carbonate), polyphosphoester, polyphosphoester urethane, poly(amino acids), polycyanoacrylates, poly(trimethylene carbonate), poly(iminocarbonate), copoly(ether-esters) (e.g. PEO/PLA), polyalkylene oxalates, polyphosphazenes, PHA-PEG, and combinations thereof. The PHA may include poly($\alpha$-hydroxyacids), poly($\beta$-hydroxyacid) such as poly(3-hydroxybutyrate) (PHB); poly(3-hydroxybutyrate-co-valerate) (PHBV); poly(3-hydroxyprionate) (PHP); poly(3-hydroxyhexanoate) (PHH), or poly(4-hydroxyacid) such as poly poly(4-hydroxybutyrate); poly(4-hydroxyvalerate); poly(4-hydroxyhexanoate), poly(hydroxyvalerate), poly(tyrosine carbonates), poly(tyrosine arylates).

In another embodiment, the hydrophilic or hydrophobic polymer useful as moiety of the copolymer comprising PC moieties is a non-degradable polymer. Representative biocompatible, non-degradable polymers include, but are not limited to, ethylene vinyl alcohol copolymer (commonly known by the generic name EVOH or by the trade name EVAL), silicones, polyolefins, polyisobutylene and ethylene-alphaolefin copolymers, styrene-isobutyl-styrene triblock copolymers, acrylic polymers and copolymers, vinyl halide polymers and copolymers such as polyvinyl chloride, poly(vinyldifluoride-co-hexafluoropropane), poly(chlorotrifluoro ethylene-co-hexafluoropropane), polyvinyl ethers such as polyvinyl methyl ether, polyvinylidene halides such as polyvinylidene fluoride and polyvinylidene chloride, polyfluoroalkenes, polyperfluoroalkenes, polyacrylonitrile, polyvinyl ketones, polyvinyl aromatics such as polystyrene, polyvinyl esters such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, alkyd resins, polyoxymethylenes; polyethers, epoxy resins, rayon, rayon-triacetate, and combinations thereof.

In a further embodiment, the hydrophobic copolymer described herein comprises one or more of the following monomers: methylmethacrylate (MMA), ethylmethacrylate (EMA), butylmethacrylate (BMA), 2-ethylhexylmethacrylate, laurylmethacrylate (LMA), or combinations thereof. By varying the copolymer's content of the hydrophobic monomers, mechanical properties such as elongation at break and toughness can be modulated. For example, a monomer having a relatively long side chain would enhance the flexibility of a coating comprising the copolymer. In contrast, a monomer having a relatively short side chain would enhance the rigidity and toughness of a coating comprising the copolymer.

In a further embodiment, the hydrophilic copolymer described herein comprises one or more of the following monomers: non-fouling monomers such as hydroxyl ethyl methacrylate (HEMA), PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), hydroxyl bearing monomers such as HEMA, hydroxypropyl methacrylate (HPMA), hydroxypropylmethacrylamide, 3-trimethylsilylpropyl methacrylate (TM-SPMA), and combinations thereof. The carboxylic acid bearing monomers or hydroxyl bearing monomers can be used to crosslink the copolymer once it is applied to the substrate to coat. This will hinder a very hydrophilic coating from dissolving away.

Lipid Molecules

In one embodiment, the lipid molecule (LI) includes phospholipids, ceramides, and cholesterol.

Phospholipids useful for making a copolymer with a hydrophilic or hydrophobic polymer can be neutral, positively charged or negatively charged synthetic phospholipids. Representative useful synthetic phospholipids include, but are not limited to, semi-synthetic phosphoryl choline such as cardiolipin or sphingosine.

In another embodiment, the phospholipids useful for making a copolymer with a biocompatible polymer can be neutral, positively charged or negatively charged natural phospholipids. Representative useful natural phospolipids include, but are not limited to, in addition to the PC moiety(ies), phosphoryl serine, phosphoryl inositol, di-phosphoryl glycerol, or zwitterionic phosphoryl ethanolamine, and combinations thereof.

In a further embodiment, the phospholipid useful for making a copolymer with a biocompatible polymer can be PC. PC is a zwitterionic functionality that mimics the outer surface of a lipid bilayer. It has good hemocompatibility, non-thrombogenicity, arterial tissue acceptance and long-term in-vivo stability. It has been used to increase the biocompatibility of polymers, especially of acrylic copolymers.

Functional Moiety F and Chemical Moiety R

In one embodiment, functional moiety F may be used to couple the hydrophilic, hydrophobic, or amphiphilic polymer to a device surface or coating comprising a chemical moiety R to which F binds or reacts.

In an embodiment, functional moiety F may be used to couple the hydrophilic, hydrophobic, or amphiphilic polymer to a protein comprising a chemical moiety R to which F binds or reacts.

In another embodiment, functional moiety F may be used to couple the hydrophilic, hydrophobic, or amphiphilic polymer to a drug delivery vehicle such as a liposome or a polymeric nanoparticle the surface of which comprises a chemical moiety R to which F binds or reacts.

Each F and R which F binds to or reacts with, forms a pair of F and R.

Examples of pairs of R and F include: amines-amine reactive esters (NHS esters, nitrophenol esters, etc); amines-aldehyde groups; amines-epoxide groups; sulfhydryl (thiols)-sulfhydryl reactive esters (NHS esters, nitrophenol esters, etc); sulfhydryl (thiols)-acrylate groups; sulfhydryl (thiols)-vinyl groups (maleimide/vinyl sulfone/vinyl ethers); sulfhydryl (thiols)-allyl groups.

Methods of Making Copolymers Comprising Phosphoryl Choline

The copolymer described herein can be synthesized by introducing the PC moiety into a polymer. The PC moieties can be introduced into the polymer via a reactive functionality, which can be, for example, hydroxyl groups, amino groups, halo groups, carboxyl groups, thiol groups, aldehyde, N-hydroxysuccinimide (NHS). Alternatively, a PC moiety can be introduced into a monomer such as an oxirane. Polymerization of the monomer can generate a polymer bearing PC moieties.

In one embodiment, a monomer bearing a protected hydroxyl functionality can be copolymerized with an oxirane, for example lactide, glycolide or caprolactone, etc., or incorporated into a polymer such as a polyester amide backbone. The hydroxyl functionality then can be deprotected and subsequently converted to a PC group. The protective group can be any of the ones that are easily removable and in addition be stable during and not interfere with the polymerization, examples include various benzyl ethers.

Reaction Scheme 1a demonstrates how to form a hydrophilic polymer which is capped at its one end by a PC moiety and the other end with a functional moiety. The polymer is allowed to react with an agent such as ethylene chlorophosphate to form an ethylene phosphate derivative of the polymer. The ethylene phosphate functionality can react with an amine to generate the PC functionality.

Reaction Scheme 1a

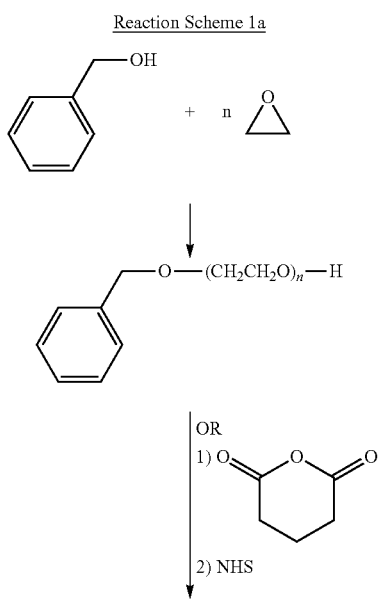

Reactions 1b and 1c represent additional methods for creating polymers useful in the present invention.

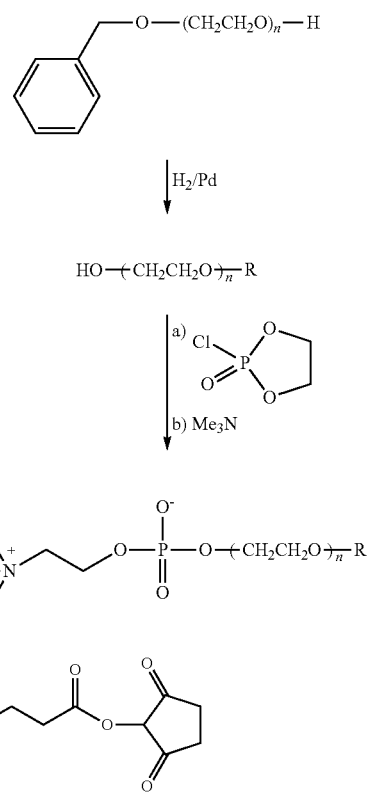

Reaction Scheme 1b

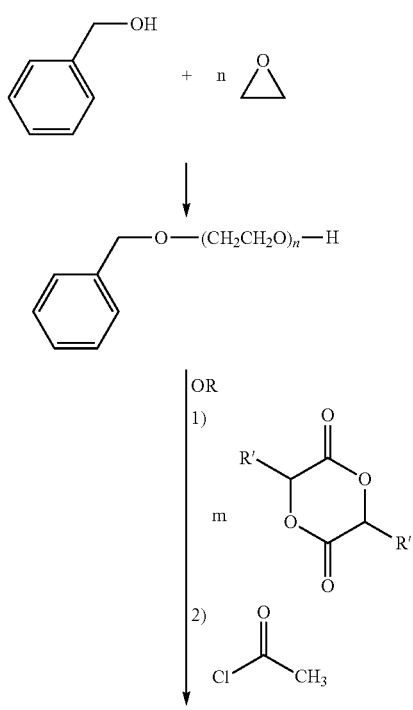

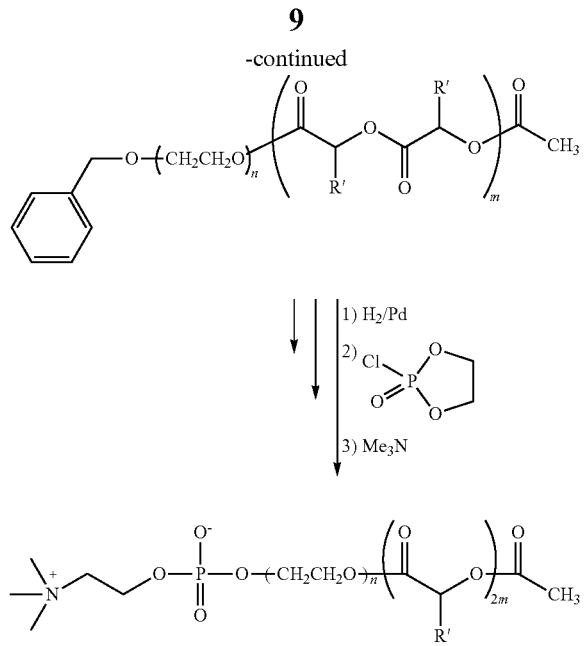

Reaction Scheme 1c

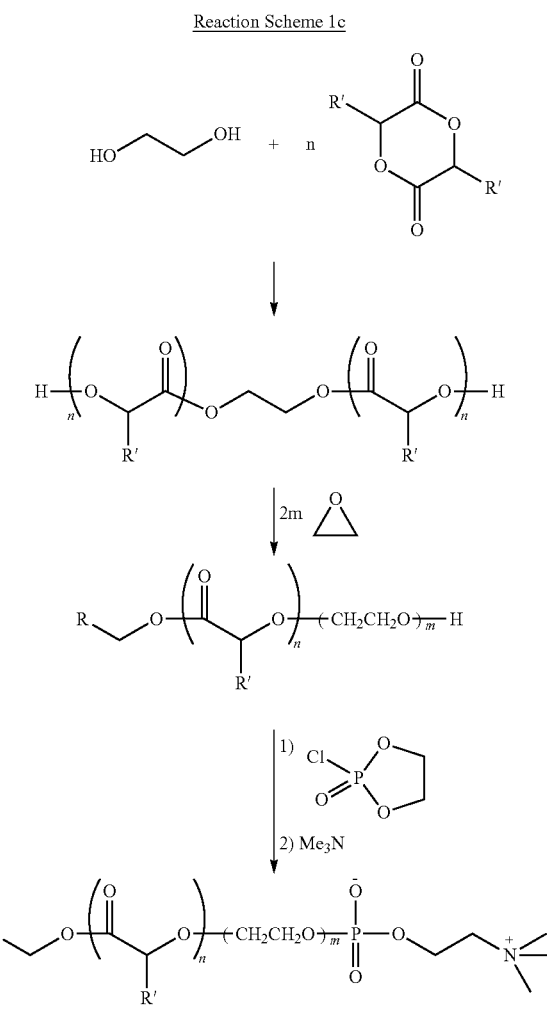

Biobeneficial Polymers

In another aspect of the present invention, the composition described herein may include one or more biobeneficial polymers including non-fouling polymers and anti-thrombogenic agents. Various non-fouling polymers are known in the art. Exemplary non-fouling polymers include PEG, polyalkene oxides, hydroxyethylmethacrylate (HEMA), poly(n-propylmethacrylamide), sulfonated polystyrene, hyaluronic acid, poly(vinyl alcohol), poly(N-vinyl-2-pyrrolidone), sulfonated dextran, and combinations thereof. Representative anti-thrombogenic moieties are heparin, salicylate (aspirin), hirudin, flavonoids, NO donor, thrombomodulin, Atrial natriuretic peptide (ANP), and combinations thereof. The non-fouling polymer can be used together with the polymers comprising phospholipid moieties as a blend or can be incorporated into the backbone of the polymers comprising phospholipid moieties.

In one embodiment, the non-fouling polymer is PEG. PEG is water-soluble and must be covalently attached to a hydrophobic backbone or to a crosslinked polymer to yield long-term benefits. PEG can readily be incorporated into the backbone of any of the copolymers by, for example, coupling the hydroxyl, amino, or carboxylic acid terminated PEG with the pendant functional groups such as carboxylic acids or hydroxyls in the backbone of the copolymer by a linking agent such as carbodiimide chemistry (1,3-dicyclohexylcarbodiimide (DCC), 1-(3-dimethylaminopropyl)-3-ethylcarbodiimide (EDC) and other Mitsunobu reagents). The PEG useful for coupling with the hydrophobic backbone of the phospholipid containing polymer has a molecular weight in the range between about 300 daltons and about 40,000 daltons.

In another embodiment, the biobeneficial polymer is heparin. Heparin is commonly used as an anti-thrombogenic agent. Heparin can be coupled via a spacer such as PEG to a polymer backbone containing functional groups such as carboxylic acids. In one embodiment, the coupling can be carried out using an aldehyde terminated heparin, which can be coupled to a PEG diamine where one amine is protected with a protective group such as t-BOC. Upon removal of the protective group, the second amine can be coupled to a carboxylic group on the polymer backbone using a linking agent such as 1,3-dicyclohexylcarbodiimide (DCC), 1-(3-dimethylaminopropyl)-3-ethylcarbodiimide (EDC) and other Mitsunobu reagents. In another embodiment, 2-(dimethylamino)ethyl methacrylate (DMAEMA) can also be incorporated into the backbone and used to ionically coordinate or conjugate with heparin.

In a further embodiment, PEG and heparin are both incorporated into the polymer comprising the phospholipid moieties. In one embodiment, a polymer having a methacrylate backbone can be made to contain 2-methacryloyloxyethylphosphorylcholine and 2-aminoethyl methacrylamide. Aldehyde terminated heparin, which is commercially available, can be coupled to the terminal amino group via reductive amination using sodium cyanoborohydride (Scheme 4).

Scheme 4

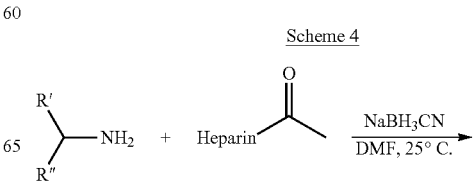

-continued $$\begin{matrix} R' \\ \diagdown \\ R'' \end{matrix} \!\!-\!\! N \!\!\diagup\!\!\begin{matrix} Heparin \\ \diagdown \\ H \end{matrix} + H_2O$$

This heparin coupling can be done either before, or after, a topcoat, comprising a polymer having a methacrylate backbone that contains 2-methacryloyloxyethylphosphorylcholine and 2-aminoethyl methacrylamide, is placed onto an implantable device such as a DES. A topcoat comprising both the PEG and heparin and a phospholipid (for example, PC) containing polymer is non-fouling and anti-thrombogenic. If desirable, other non-fouling and/or anti-thrombogenic moieties can be incorporated into the topcoat.

Bioactive Agents

The bioactive agent can be any agent which is biologically active, for example, a therapeutic, prophylactic, or diagnostic agent. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 or more grams per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. Representative diagnostic agents are agents detectable by x-ray, fluorescence, magnetic resonance imaging, radioactivity, ultrasound, computer tomography (CT) and positron emission tomography (PET). Ultrasound diagnostic agents are typically a gas such as air, oxygen or perfluorocarbons.

In the case of controlled release of agents, a wide range of different bioactive agents can be incorporated into a controlled release device. These include hydrophobic, hydrophilic, and high molecular weight macromolecules such as everolimus and proteins. The bioactive compound can be incorporated into polymeric coating in a percent loading of between 0.01% and 70% by weight, more preferably between 5% and 50% by weight.

In one embodiment, the bioactive agent can be for inhibiting the activity of vascular smooth muscle cells. More specifically, the bioactive agent can be aimed at inhibiting abnormal or inappropriate migration and/or proliferation of smooth muscle cells for the inhibition of restenosis. The bioactive agent can also include any substance capable of exerting a therapeutic or prophylactic effect in the practice of the present invention. For example, the bioactive agent can be for enhancing wound healing in a vascular site or improving the structural and elastic properties of the vascular site. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, zotarolimus, dexamethasone, clobetasol, paclitaxel, estradiol, 4-amino-2,2,6,6-tetramethylpiperidine-1-oxyl (4-amino-TEMPO), 4-hydroxy-2,2,6,6-tetramethylpiperidine-1-oxyl (TEMPOL), tacrolimus, sirolimus, sirolimus derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, prodrugs, co-drugs, and a combination thereof. The foregoing substances are listed by way of example and are not meant to be limiting. Other active agents which are currently available or that may be developed in the future are equally applicable.

Useful bioactive agents also include prodrugs and co-drugs of the agents described herein.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent required to inhibit the desired cellular activity of the vascular region can depend upon factors such as the particular circumstances of the patient; the nature of the trauma; the nature of the therapy desired; the time over which the administered ingredient resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Coating Constructs

The copolymers described herein can be used to form coating compositions for coating on an implantable device, for example, a drug-eluting stent (DES). The copolymer comprising at least one PC moiety can be used alone or in combination with another polymer. For use as DES coatings, the composition can include a bioactive agent.

The coatings described herein can have various configurations. In one embodiment, the coating can be formed with the copolymer described herein alone or in combination with other polymers. Useful other polymers include the degradable and non-degradable biocompatible polymers described above. The copolymers described herein can be used to form a topcoat on DES on top of a drug reservoir coating that does not contain the copolymers comprising the PC moieties. For example, a DES can be made to have a coating that has a primer layer comprising a polymer such as poly(n-butyl methacrylate) (PBMA), a drug reservoir layer comprising a biocompatible, biodegradable or non-degradable polymer as described above with no phospholipid moieties such as ethylene vinyl alcohol (EVAL) or polyvinylidene fluoride (PVDF), and finally a topcoat with a copolymer described herein that comprises PC moieties. The topcoat may further comprise a polymer with no PC moieties such as PBMA.

In another embodiment, the coating may comprise a copolymer comprising phospholipids moieties in all the layers of the coating. For example, a DES coating can be formed to have a primer layer that comprises about 1-5 wt % PBMA-PC, a layer of reservoir that comprises PBMA and about 1-20 wt % PBMA-PC, and a topcoat that comprises PBMA and 25-50 wt % PBMA-PC.

In another embodiment, the coating can be made to comprise layers having a copolymer that comprises PC moieties in a concentration gradient in the various layers with a concentration of the copolymer that is higher in the topcoat, decreasing to the lowest concentration in the primer layer. For example, the copolymer can be PBMA-PC.

In a further embodiment, the coating construct can be made to release two or more drugs. In one embodiment, if desirable, the second drug can be blended into the matrix with the first drug such as zotarolimus or everolimus such that the second drug can be released in the same time frame with the first drug. In another embodiment, if the second drug is hydrophilic and it is desirable to have a quick release of the second drug, it can be blended with the topcoat comprising phospholipid moieties such as PC moieties. Such hydrophilic drugs include peptides such as cyclic RGD, aspirin, nitric oxide donors, and stable nitroxides, etc. The second drug can also be swell-loaded into the applied topcoat. Additional drugs can be loaded onto the coat in the drug reservoir or topcoat.

Methods of Using the Coating Composition

The coating composition can be coated onto any implantable device by any established coating process, e.g., a spray process. Generally, the coating process involves dissolving or suspending the composition in a solvent to form a solution or a suspension of the coating composition, and then applying the solution or suspension to an implantable device such as a DES.

As used herein, an implantable device may be any suitable medical substrate that can be implanted in a human or veterinary patient. A preferred implantable device is DES. Examples of stents include self-expandable stents, balloon-expandable stents, and stent-grafts. Other exemplary implantable devices include grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

The coating compositions of the present invention may also be coated onto non-implantable devices, such as angioplasty balloons and other devices that deliver implantable devices.

EXAMPLES

The embodiments of the present invention will be illustrated by the following set forth examples. All parameters and data are not to be construed to unduly limit the scope of the embodiments of the invention.

Example 1A

P(MPC-PEGA-BMA) Copolymer

The components, 2-methacryloyloxyethyl phosphorylcholine (MPC), butylmethacrylate (BMA), poly(ethylene glycol) acrylate (PEGA) (Mn=350 Da) and AIBN (α,α'-azobutyronitrile) may be dissolved in ethanol at a molar ratio of (15:10:74:0.5). The reactants are maintained at 62° C. for 24 h. The polymer may be purified, by a double precipitation in cold methanol, to yield a white powder.

A first composition may be prepared by mixing the following components:
(a) about 2 mass % poly(butyl methacrylate) (PBMA);
(b) dissolved in a mixture of acetone and cyclohexanone (30% and 70% respectively).

The first composition may be applied onto the surface of a bare 12 mm VISION stent (available from Abbott Vascular) by spraying and drying to form a stent coating. A spray coater may be used, having a 0.014 fan nozzle maintained at ambient temperature with a feed pressure of about 0.2 atm (about 3 psi) and an atomization pressure of about 1.3 atm (about 20 psi). About 20 μg of the wet coating may be applied per pass. Between the passes, the coating may be dried at about 50° C. for about 10 seconds. Following the last pass, the coating may be baked at about 50° C. for about 1 hour, yielding a dry primer layer. The dry primer layer would contain about 80 μg of PBMA.

A second composition may be prepared by mixing the following components:
(a) about 2 mass % p(MPC-PEGA-BMA); and
(b) about 0.7 mass % everolimus; and
(c) the balance, a mixture of acetone and dimethylformamide (50% and 50% respectively).

The second composition may be applied onto the dry reservoir layer using the same coating technique and conditions as for making the primer layer, yielding a dry topcoat layer. The dry topcoat layer contains about 100 μg of p(MPC-PEGA-BMA).

16 stents may be coated as described above. 8 stents may be sterilized using electron beam sterilization at a dose of 25 KGy as known to those having ordinary skill in the art, and the other 8 stents may not be sterilized.

Example 1B

P(MPC-PEGA-BMA) Copolymer

A first composition may be prepared by mixing the following components:
(a) about 2 mass % p(MPC-PEGA-BMA); and
(b) about 0.7 mass % everolimus; and
(c) the balance, a mixture of acetone and dimethylformamide (50% and 50% respectively).

The composition may be applied onto the surface of a bare 12 mm VISION stent (available from Abbott Vascular) by spraying and drying to form a stent coating. A spray coater may be used, having a 0.014 fan nozzle maintained at ambient temperature with a feed pressure of about 0.2 atm (about 3 psi) and an atomization pressure of about 1.3 atm (about 20 psi). About 20 μg of the wet coating may be applied per pass. Between the passes, the coating may be dried at about 50° C. for about 10 seconds. Following the last pass, the coating may be baked at about 50° C. for about 1 hour, yielding a dry coating layer. The dry coating contains about 100 μg of P(MPC-PEGA-BMA).

16 stents may be coated as described above. 8 stents may be sterilized using electron beam sterilization at a dose of 25 KGy as known to those having ordinary skill in the art, and the other 8 stents may not be sterilized.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A polymer having the following structure:

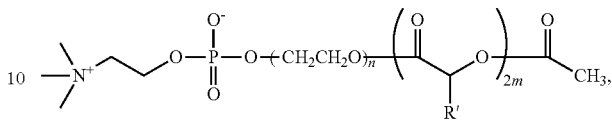

wherein: n and m are independently an integer; R' is H or CH$_3$.

2. The polymer of claim 1, further comprising a therapeutic agent selected from a group consisting of proteins, peptides, anti-inflammatory agents, antivirals, anticancer drugs, anticoagulant agents, free radical scavengers, steroidal anti-inflammatory agents, antibiotics, nitric oxide donors, super oxide dismutases, super oxide dismutases mimics, cytostatic agents, prodrugs thereof, co-drugs thereof, and a combination thereof; or the drug selected from a group consisting of zotarolimus, dexamethasone, clobetasol, paclitaxel, estradiol, 4-amino-2,2,6,6-tetramethylpiperidine-1-oxyl (4-amino-TEMPO), 4-hydroxy-2,2,6,6-tetramethylpiperidine-1-oxyl(TEMPOL), tacrolimus, sirolimus, sirolimus derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, prodrugs thereof, co-drugs thereof, and combinations thereof.

3. An implantable device comprising a coating that comprises the polymer of claim 2.

4. A coating composition comprising the polymer of claim 1.

5. A method of treating a human being by implanting in the human being a stent as defined in claim 3,
wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

6. An angioplasty balloon including a coating that comprises the polymer of claim 2.

* * * * *